(12) United States Patent
Henriksson et al.

(10) Patent No.: US 9,445,882 B2
(45) Date of Patent: Sep. 20, 2016

(54) VAGINAL DEVICE

(75) Inventors: Lars Henriksson, Vellinge (SE); Jan Clarén, Lund (SE)

(73) Assignee: Invent Medic Sweden AB, Hässleholm (SE)

( * ) Notice: Subject to any disclaimer, the term of this patent is extended or adjusted under 35 U.S.C. 154(b) by 377 days.

(21) Appl. No.: 13/141,226

(22) PCT Filed: Dec. 17, 2009

(86) PCT No.: PCT/SE2009/051438
§ 371 (c)(1),
(2), (4) Date: Aug. 19, 2011

(87) PCT Pub. No.: WO2010/074635
PCT Pub. Date: Jul. 1, 2010

(65) Prior Publication Data
US 2011/0295058 A1    Dec. 1, 2011

Related U.S. Application Data

(60) Provisional application No. 61/139,742, filed on Dec. 22, 2008.

(30) Foreign Application Priority Data

Dec. 22, 2008    (SE) ..................................... 0850172

(51) Int. Cl.
A61F 2/00    (2006.01)

(52) U.S. Cl.
CPC ..................................... A61F 2/005 (2013.01)

(58) Field of Classification Search
CPC .... A61F 2/0036; A61F 2/005; A61F 2/0009; A61F 2/04; A61F 6/08; A61F 2250/0007; A61F 2250/0031; A61F 2002/047; A61F 2250/0002; A61F 2/0027; A61F 2/0045; A61B 2017/00805

USPC ........... 600/29–32; 128/885, 830, 834, 838; 604/279, 515, 517
See application file for complete search history.

(56) References Cited

U.S. PATENT DOCUMENTS 4,873,996 A    10/1989  Maurer
5,081,985 A *   1/1992  Borodulin et al. ............... 601/1
(Continued)

FOREIGN PATENT DOCUMENTS

FR    2228464 A1    12/1974
FR    2228464       4/1976
(Continued)

OTHER PUBLICATIONS

European Office Action for European Application No. 09835346.9 dated May 9, 2016 in 3 pages.

*Primary Examiner* — Christine H Matthews
(74) *Attorney, Agent, or Firm* — Knobbe, Martens, Olson & Bear LLP (57) ABSTRACT

The present invention refers to a vaginal device of an elastic material, the vaginal device comprising a longitudinal portion having a geometrical center line, an upper end and a lower end and which vaginal device is intended to be inserted securely fixated inside of a vagina, the upper end being the innermost of the vaginal device in the vagina during use, to support against the urethra, through the vaginal wall, to prevent urinary stress incontinence in a woman, wherein the vaginal device comprises at least one supporting portion protruding from the longitudinal portion and a reference member protruding from the longitudinal portion at the lower end, which reference member during use is fixated against the vaginal introitus, holding the vaginal device securely fixated inside of the vagina and ensuring the at least one supporting portion to support against the urethra.

24 Claims, 2 Drawing Sheets

(56) References Cited

U.S. PATENT DOCUMENTS

| | | | |
|---|---|---|---|
| 5,360,402 A * | 11/1994 | Conway et al. | 604/97.01 |
| 5,609,559 A | 3/1997 | Weitzner | |
| 5,640,976 A * | 6/1997 | Levius | 128/885 |
| 5,996,585 A * | 12/1999 | Migachyov | A61F 2/0022 128/885 |
| 6,110,099 A * | 8/2000 | Benderev | 600/30 |
| 6,135,945 A | 10/2000 | Sultan | |
| 6,470,890 B1 * | 10/2002 | Diokno et al. | 128/885 |
| 6,645,137 B2 | 11/2003 | Ulmsten et al. | |
| 6,739,340 B1 | 5/2004 | Jensen et al. | |
| 8,360,954 B2 * | 1/2013 | Kim | 600/29 |
| 8,435,168 B2 * | 5/2013 | Ziv et al. | 600/29 |

FOREIGN PATENT DOCUMENTS

| | | |
|---|---|---|
| GB | 2090144 | 7/1982 |
| GB | 2146901 | 5/1985 |
| WO | WO 98/49980 | 11/1998 |

* cited by examiner

VAGINAL DEVICE

This is a National Phase Application filed under 35 U.S.C. 371 as a national stage of PCT/SE2009/051438, filed on Dec. 17, 2009, an application claiming the benefit from Swedish Application No. 0850172.8, filed on Dec. 22, 2008, and claiming the benefit under 35 U.S.C. 119(e) from U.S. Provisional Application No. 61/139,742, filed on Dec. 22, 2008, the entire content of each of which is hereby incorporated by reference in its entirety.

FIELD OF THE INVENTION

The present invention relates to a vaginal device intended as an aid for women suffering from urinary stress incontinence.

BACKGROUND OF THE INVENTION

Urinary incontinence is a public health issue which affects more than 13 million women in the USA only. There exist different types of urinary incontinence in women, such as urge incontinence, stress incontinence and mixed incontinence. Women having urge incontinence suffer from at least some unwanted leakage caused by urgency. The focus herein is however not urge incontinence but urinary stress incontinence, often also just called stress incontinence. Of the number of women suffering from urinary incontinence about half of them suffer from stress incontinence. Urinary stress incontinence is mainly caused by connective tissue laxity or damage in the vagina or its supporting ligaments. The background to urinary stress incontinence and its origin may be described by the Integral Theory (An integral theory and its method for the diagnosis and management of female urinary incontinence, Petros P E, Ulmsten U I, Scand J Urol Nephrol Suppl, 1993; 153:1-93), which states that connective tissue damage to the 3 zones of the Integral System, which encompasses all three pelvic organs, bladder, vagina and ano-rectum, is the ultimate cause of prolapse and dysfunction in these organs. In other words, stress incontinence may be caused by a defect function of the tissue or ligaments connecting the urethra and vaginal wall with the pelvic muscles and pubic bone. Examples of women suffering from stress incontinence are such having experienced complicated deliveries, such as disproportion, big child or instrumental delivery. However, genetic factors may also be of importance and may cause these defect functions.

Today there exist surgical methods supported by the knowledge of the Integral Theory. For example, U.S. Pat. No. 5,899,909 discloses a surgical method for restoration of incontinence, the today called TVT (tension free vaginal tape) method which is a method effectively preventing and eliminating stress incontinence. U.S. Pat. No. 5,899,909 discloses a method comprising the steps of passing a tape into the body via the vagina first at one end thereof and then at the other end thereof at one side and the other, respectively, of urethra to form a loop around urethra, located between urethra and the upper vaginal wall, extending said tape over the pubic bone and through the abdominal wall, the ends of the tape being available outside the abdominal wall, tightening said strap at said ends, and leaving the tape implanted in the body. The tape is left permanently in the body to provide itself, as an artificial ligament, the reinforcement of the tissue required in order to restore the urinary incontinence, and/or to provide said reinforcement by the development of fibrous tissue. A surgical instrument for performing the method according to U.S. Pat. No. 5,899,909 is also disclosed.

The method disclosed according to U.S. Pat. No. 5,899,909 works very well. However, it is a surgical method and as such it is not available for all women in need of help to reduce or eliminate stress incontinence problems. Due to the fact that stress incontinence in women is an extensive, widely spread problem all around the world, it is firstly not possible to treat everyone in need of a surgical treatment. Secondly, in several countries, such as China and India, the possibility of receiving a TVT surgery is very limited. Moreover, many women suffering from stress incontinence prefer conservative treatment or are not suitable for TVT surgery, for instance due to high age. Furthermore, in countries not having free medical service, or with only parts of that service being free, there will be many women having this problem but not the financial means to pay for a TVT surgery.

There exist today different devices with the purpose of alleviating incontinence in women. U.S. Pat. No. 6,739,340 discloses a device for prevention of involuntary urination. The device comprises a body for arrangement in the vagina for compressive action on and support of the neck of the bladder and optionally the urethra. The body has a substantially elongated shape with a longitudinal axis extending, in the intended direction of insertion, from a proximal to a distal end and is made from a compressive and elastically deformable material. The body comprises at least one part protruding from the outer surface of the body which is said to provide at least one pressure area for contact with the neck of the bladder and optionally the urethra.

U.S. Pat. No. 6,645,137 discloses a vaginal insert having a flexible body either in the form of a belt or a split cylinder. In either case, the insert may be coiled into a coiled state. The body is said to have a reduced diameter when coiled and exhibits a resilient bias toward uncoiling and expanding in diameter from the coiled state. When the insert is inserted into the vagina of a patient, it is said to expand and press against the vaginal wall, such as for treating incontinence. A medicament may be combined with the insert that is introduced to the patient through contact with the insert, such as for treating incontinence with a drug as well as pressure. The belt-type body may incorporate mating ridges and grooves to keep the insert in a cylindrical shape. Latch elements may be incorporated on the insert to support the insert in an expanded, partially uncoiled state.

There are disadvantages with the known vaginal devices disclosed above. Firstly, none of these devices are securely fixated inside of the vagina during normal use. When women move or for instance exercise there exists a great risk for movement of these devices inside the vagina. Another circumstance when this problem may be extensive is during a sneeze when the pressure power inside of the vagina is very large. This may also render the vaginal devices being pushed down towards the opening of the vagina. These cases of movement of the vaginal devices inside of the vagina render the pressing elements, that is the at least one protruding part in U.S. Pat. No. 6,739,340 and the protruding coils in U.S. Pat. No. 6,645,137, of the vaginal devices to press on the wrong site of the vaginal wall or urethra. In those cases these vaginal devices have only limited effect or no effect at all with respect to the prevention of stress incontinence. Moreover, both of these devices may be harmful for the patient or be perceived as unpleasant to use. This is caused by the designs of the pressing elements of these vaginal devices.

One object of the present invention is to provide a vaginal device for the prevention of incontinence of the type called urinary stress incontinence, which vaginal device may function as an alternative for a patient not suitable for or one does not want to undergo a TVT surgery and which vaginal device solves the problems described above with up to now known vaginal devices.

SUMMARY OF THE INVENTION

The object above is solved by a vaginal device of an elastic material, said vaginal device comprising a longitudinal portion having a geometrical centre line, an upper end and a lower end and which vaginal device is intended to be inserted securely fixated inside of a vagina, the upper end being the innermost of the vaginal device in the vagina during use, to support against the urethra, through the vaginal wall, to prevent urinary stress incontinence in a woman, wherein the vaginal device comprises at least one supporting portion protruding from the longitudinal portion, said at least one supporting portion being intended to support against the urethra, through the vaginal wall, at a site located between close to the maximal urethral pressure point and the bladder neck, and wherein the vaginal device also comprises a reference member protruding from the longitudinal portion at the lower end, which reference member during use is fixated against the vaginal introitus, holding the vaginal device securely fixated inside of the vagina and ensuring said at least one supporting portion to support against the urethra, through the vaginal wall, at the intended site located between close to the maximal urethral pressure point and the bladder neck.

As is mentioned above, during use, said at least one supporting portion of the vaginal device according to the present invention is intended to support against the urethra, through the vaginal wall, at a site located between close to the maximal urethral pressure point and the bladder neck. The maximal urethral pressure point of the urethra is situated close to the middle point of the urethra or the mid urethra as it is also called. When a woman is about to sneeze or cough, the pressure built up along the urethra is the highest at this maximal urethral pressure point where the muscular pressure gets additional forces from the bending of the proximal portion of urethra in downward direction at the "urethral knee". The fixation of the distal portion of a normal urethra at the "urethral knee" is due to the support from the posterior urethral ligaments on both sides of the urethra which connect the symphysis pubis with the urethra and the anterior vaginal wall. Due to compression of the urethra and a "curtsy effect" of the "urethral knee" during a pressure built up due to e.g. sneezing or coughing, this area is important to support so that the depression of the "urethral knee" decreases. This is accomplished by the at least one supporting portion of the vaginal device according to the present invention. Preferably, said at least one supporting portion according to the present invention supports against the urethra, through the vaginal wall, against the maximal urethral pressure point or very close to it. At this site, the maximal effect is obtained. According to the present invention, however, said at least one supporting portion may also support at sites between close to the maximal urethral pressure point and the bladder neck, such as at several sites. Moreover, the expression "close to the maximal urethral pressure point" should in this case be interpreted as possible sites on both sides of the maximal urethral pressure point, and not only on that side facing towards the bladder neck.

The supporting portion of the vaginal device according to the present invention will support the lax urethra, through the vaginal wall, in cases of stress incontinence caused by laxity of the posterior urethral ligaments. In rest there will be no or very little compression of the urethra, which can interfere with the blood circulation. This is also important due to the fact that the vaginal device according to the present invention should be comfortable to use. This is also a difference in comparison to vaginal devices according to state of the art which are stated to press against the urethra through the vaginal wall. Furthermore, the at least one supporting portion according to the present invention must be designed to be able to support the urethra at times when the pressure built up is very high, such as when a woman is about to sneeze. This supporting feature of the vaginal device according to the present invention requires that the at least one supporting portion is flexible in its nature, both in terms of material and construction, but also able to support the urethra at the intended site when the pressure wave along the urethra is large.

Another very important difference of the vaginal device according to the present invention in comparison to known devices is the reference member of the present invention. The reference member protrudes from the longitudinal portion at the lower end and is fixated against the vaginal introitus. The reference member fixates the vaginal device in place so that the at least one supporting portion supports the urethra at the intended site. This reference member is of great importance. When women are moving there is an evident risk for vaginal devices to slide out of place inside of the vagina. In such a case, when and if a pressure wave arises from the abdomen, such as when sneezing or coughing, the vaginal device will not be fixated at the right place. This problem is solved by the vaginal device according to the present invention, having the reference member making sure that the vaginal device and hence at least one supporting portion to be fixated to support the urethra, through the vaginal wall, at the intended site.

Moreover, the fixation of the reference member against the vaginal introitus is also of importance. The tissue against and around the vaginal introitus (labium minorae and majorae) shall be able to close around the reference member, so that the reference member and vaginal device are fixated securely. This means that the fixation is made so that the reference member is positioned at the labia minora, against the vaginal introitus, and not the labia majora. Due to the fact that labia majora comprises fatty tissue and the size of the labia majora differs a lot from woman to woman, it is difficult to design a reference member for fixation outside the labia majora. After the fixation, tight pair of briefs and possibly additional net pants will ensure that the fixated vaginal device according to the present invention is secured in place.

The vaginal device according to the present invention may have different design. For example, the at least one supporting portion does not have to protrude around the longitudinal portion. It is, however, important that the at least one supporting portion of the vaginal device protrudes in the intended direction towards the urethra during use. As long as the at least one supporting portion is possible to support against the urethra, through the vaginal wall, the design thereof may vary. If the longitudinal portion has a larger diameter it is possible to design the vaginal device so that the longitudinal portion in fact supports against the vaginal wall. In such a case, the at least one supporting portion shall not protrude in all directions from the longitudinal portion, that is, shall not protrude around the longitudinal portion, due to the fact that the vaginal device as a whole in that case would not be able to be inserted in the vagina, or at least would not be comfortable to use. In such a case, the at least one supporting portion may e.g. have a half-moon shape or the like so that the supporting portion only protrudes in an intended direction against the urethra. Many other shapes of the at least one supporting portion are also possible, such as flower-shaped and protruding around the longitudinal portion, protruding around the longitudinal portion asymmetrically, but of course also a circular shaped disc which hence protrudes symmetrically around the longitudinal portion. In the latter case, the diameter of the longitudinal portion of course is smaller in comparison with the case of a half-moon shaped supporting portion due to the fact that the at least one supporting portion protrudes around the longitudinal portion and as such bears against the vaginal wall in all directions.

DETAILED DESCRIPTION OF THE INVENTION

As is mentioned above, the vaginal device according to the present invention is made of an elastic material. The degree of hardness of materials possible to use for the vaginal device may be measured by shore A. Examples of possible materials may e.g. have a shore A of 10-50, e.g. 10-40, 10-30, 20-40 or 20-30. According to another specific embodiment of the present invention, the vaginal device is made of an elastic material of medical quality, that is an inert material. Furthermore, the material may be roentgen visualised. The latter may be of interest so that the vaginal device is visible for X-ray examination so that it is possible to see where the vaginal device according to the present invention supports the urethra, through the vaginal wall. Examples of possible elastic materials, that is elastic tissue accepted inert materials, are polyurethane, silicone rubber, latex rubber, polystyrene copolymer materials and natural rubber, or combinations thereof. Other elastic tissue accepted inert materials are of course also possible to use.

As is mentioned above, the design of the supporting portion according to the present invention may vary, but the important characteristic of the portion is the supporting feature. According to one embodiment, the at least one supporting portion is resilient in a radial direction towards the urethra through the vaginal wall. This implies that the supporting portion during support of the urethra, through the vaginal wall, may fold itself somewhat in a radial direction, that is fold longitudinal to the longitudinal portion. This may be of interest due to the fact that this may give an optimized support to the urethra without pressing to hard on the vaginal wall, and consequently the vaginal wall will not be damaged by ischaemia. Moreover, it may also give an increased comfort for the user in comparison to the known vaginal devices. The possible radial resilience towards the urethra through the vaginal wall according to the present invention is also something that differs from the known vaginal devices, which only may give resilience in an axial direction towards the urethra through the vaginal wall. This may be observed by looking at the drawings of U.S. Pat. No. 6,739,340, showing at least one rigid pressing member of the device which pressing member only is resilient due to use of a flexible material, as well as U.S. Pat. No. 6,645,137, which discloses pressing rigid rings of a similar type as is disclosed according to U.S. Pat. No. 6,739,340.

The at least one supporting portion according to the present invention may, however, also be of a more rigid type, such as the ones disclosed according to U.S. Pat. No. 6,739,340 and U.S. Pat. No. 6,645,137. The choice of the elastic material and the hardness thereof of the vaginal device are important in this sense. A thick at least one supporting portion is e.g. possible according to the present invention if a soft elastic material having a low hardness (shore A) is chosen for the vaginal device. This gives a supporting portion which is not resilient in a radial direction towards the urethra through the vaginal wall, but due to the choice of a soft elastic material, the supporting portion will give both enough support to the urethra, through the vaginal wall, and still be harmless to the vaginal wall and comfort to use. The choice of the design of the at least one supporting portion according to the present invention depends in other words on several parameters, such as if only one supporting portion is intended, the material of the vaginal device and hence supporting portion or portions and the thickness and material thereof.

As mentioned above, the design of the at least one supporting portion may vary. According to one specific embodiment of the present invention, the at least one supporting portion protrudes all around the longitudinal portion. This implies that the at least one supporting portion or supporting member e.g. may look like flower-shaped or like a circular disc if the vaginal device is viewed from above. According to another specific embodiment of the present invention, the at least one supporting portion protrudes all around the longitudinal portion and is substantially circular in a plane perpendicular to the geometrical centre line. This implies a disc-like supporting portion disclosed above.

Moreover, the vaginal device according to the present invention may be provided with some specific features. According to one specific embodiment, the vaginal device of the present invention comprises at least one perforation going through the at least one supporting portion. This at least one perforation may be provided as an outflow cavity for possible menstrual blood inside of the vagina.

The size of the different parts of the vaginal device may vary. For example, the diameter of the vaginal device, especially at its widest place, may vary. This is due to the fact that the size of vaginas of women may vary. Therefore, according to one specific embodiment, the at least one supporting portion protrudes all around the longitudinal portion, is substantially circular in a plane perpendicular to the geometrical centre line and has a diameter of 25-45 mm, such as 25-40 mm, 25-35 mm, 30-45 mm, 30-35 mm, 35-45 mm, 35-40 mm, 40-45 mm. Examples of some possible diameters are 30, 35 and 40 mm. Although this embodiment discloses at least one supporting portion or supporting member being substantially circular, other shapes are possible as well, such as the flower-shaped supporting portion mentioned above. In such a case, the diameter should be interpreted as the length from a most protruding point of the supporting portion on one side of the longitudinal portion to another most protruding point of the supporting portion on the other side of the longitudinal portion, through a geometrical centre inside of the longitudinal portion.

As said above, the diameter of the longitudinal portion may vary, dependent inter alia on if the supporting portion is protruding all around the longitudinal portion. According to one specific embodiment of the present invention, the longitudinal portion is circular and has a diameter of 10-20 mm, such as 10-15 mm, 15-20 mm, e.g. 15 mm. A substantially circular cross section of the longitudinal portion is advantageous due to the fact of a better fit inside of the vagina.

The length of the vaginal device may also vary. However, there exists a lower possible threshold due to the fact that the vaginal device should make it possible for the supporting portion to support at the possible intended sites of the urethra. An upper limit exists also due to obvious reasons. This upper limit is about 90 mm due to the fact that the normal length of the vagina up to the anterior fornix is about that length in rest. According to one specific embodiment of the present invention, the longitudinal portion has a length of 50-90 mm from the lower end to the upper end, such as 50-80 mm, 60-80 mm, e.g. 70 mm. According to one embodiment, the upper end has a round shape and has a distance of 10-45 mm to the uppermost of the at least one supporting portion, at the geometrical centre line. This distance depends on the full length of the longitudinal portion from the lower end to the upper end. According to yet another specific embodiment of the present invention, the distance from the lower end of the longitudinal portion to the centre of the lowermost of the at least one supporting portion, at the geometrical centre line, is 20-55 mm, such as 20-50 mm, 20-45 mm, 20-40 mm, 20-35 mm, 20-30 mm, 20-25 mm, 25-55 mm, 25-50 mm, 25-45 mm, 25-40 mm, 25-35 mm, 25-30 mm, 30-55 mm, 30-50 mm, 30-45 mm, 30-40 mm, 30-35 mm, 35-50 mm, 35-45 mm, 35-40 mm, 40-55 mm, 40-50 mm, 40-45 mm, 45-55 mm, 45-50 mm, 50-55 mm, e.g. 20 mm, 25 mm, 30 mm, 35 mm, 40 mm or 45 mm.

The vaginal device according to the present invention may further be provided with additional features. According to one embodiment, the longitudinal portion is hollow from the lower end towards the upper end, but not through the upper end. This may be of interest when the vaginal device is intended to use in a kit together with some kind of introducible probe, rod or plug or the like, which should be possible to insert into the cavity of the hollow vaginal device to give different properties. If the longitudinal portion is hollow, the wall of the longitudinal portion, from the inside to the outside, should be thin enough so that the properties of the introducible probe, rod or plug or the like is possible to afford to the vaginal device. As an example, if the introducible is a rod intended to give a higher hardness to the longitudinal portion of the vaginal device, the wall of the vaginal device must be thin enough for the harder rod to give a high hardness to the longitudinal portion.

Moreover, as said, the thickness of the at least one supporting portion may vary. According to one embodiment of the present invention, the at least one supporting portion has a thickness of 3-5 mm, such as 3-4 mm, 4-5 mm, e.g. 4 mm. The thickness of the supporting portion is by definition the thickness in a direction which is perpendicular to the protrusion of the supporting portion from the longitudinal portion.

According to the present invention, there may be provided more than one supporting portion or supporting member along the longitudinal portion. Therefore, according to one specific embodiment of the present invention, the vaginal device comprises at least two supporting portions protruding from the longitudinal portion, said at least two supporting portions protruding separately from each other along the longitudinal portion and all of the at least two supporting portions being intended to support against the urethra, through the vaginal wall, at sites located between close to the maximal urethral pressure point and the bladder neck. According to one embodiment of the present invention, the vaginal device comprises two supporting portions protruding from the longitudinal portion, wherein the two supporting portions protrude separately from each other along the longitudinal portion. The distance between the two supporting portions or supporting members may in this specific case vary, but as an example the distance between these two may be about 8-12 mm, such as 9-11 mm, such as about 10 mm, from a geometrical middle point of the uppermost supporting portion to a geometrical middle point of the lowermost supporting portion. This distance corresponds to that of the vaginal tape used in a TVT surgery, and with two supporting portions which are resilient in a radial direction towards the urethra through the vaginal wall, circularly shaped and hence protruding around the entire longitudinal portion, these may together support the urethra, through the vaginal wall, at the same site of the urethra as the TVT tape stabilises. To achieve this effect and to achieve an elevated resilient effect, it may be advantageous to provide two supporting portions, in the shape of circular discs described above, which protrude separately from each other along the longitudinal portion and which have a thickness of about 4 mm. The diameter of these discs may e.g. be 30, 35 or 40 mm, the distance from the lower end of the longitudinal portion to the lowermost of the two supporting portions may be 40-50 mm, such as 45 mm, along the geometrical centre line, the distance between the lowermost of the two supporting portions and the uppermost of the two supporting portions may e.g. be about 8-12 mm, such as 10 mm, from the geometrical centre of the lowermost of the two to the uppermost, at the centre line, and the defined thickness of the two supporting portions may be 3-5 mm, such as about 4 mm. Moreover, the longitudinal portion may be hollow as is disclosed above.

According to one specific embodiment of the present invention, the vaginal device comprises two supporting portions protruding from the longitudinal portion, said at least two supporting portions protruding separately from each other along the longitudinal portion and both of the at least two supporting portions being intended to support against the urethra, through the vaginal wall, at two sites located between close to the maximal urethral pressure point and the bladder neck, and wherein the distance from the lower end of the longitudinal portion to the centre of the lowermost of the two supporting portions, at the geometrical centre line, is 20-50 mm, such as 25-45 mm, 30-45 mm, 35-50 mm, 35-35 mm, e.g. 40 mm or 45 mm, and the distance from the lower end of the longitudinal portion to the centre of the uppermost of the two supporting portions, at the geometrical centre line, is 50-65 mm, such as 50-60 mm, e.g. 55 mm.

The design of the reference member according to the present invention may also vary. According to one specific embodiment, the reference member has a right protruding end and optionally a left protruding end, the right protruding end protruding at least 40 mm from the geometrical centre line of the longitudinal portion at the lower end and the left protruding end protruding below 25 mm, such as e.g. 10-25 mm, 10-20 mm, 15-25 mm, e.g. 15 mm, from the geometrical centre line of the longitudinal portion at the lower end.

The meaning of the right protruding end and left protruding end of the reference member may be understood by viewing the accompanied drawings. The right protruding end of the reference member is that end that will be fixated against the perineum by the user, and if done, the left protruding end of the reference member is that end facing towards the opposite direction, that is towards the clitoris but not reaching the same. This is the reason for the different length thresholds for the right and left protruding end, respectively. About 40 mm or some above has proven to be a functional length for the right protruding end of the reference member from the centre line of the longitudinal portion so that the reference member is possible to fixate against the perineum by the user in a functional way. The left protruding end of the reference has as mentioned a length below 25 mm from the centre line of the longitudinal portion. This is due to that the left protruding end should be short enough not to irritate the clitoris of a female user. However, even if a vaginal device according to the present invention without a left protruding end of the reference member is possible, such a left protruding end may increase the stability and hence fixation of the entire vaginal device inside of the vagina during use. Without the left protruding end of the reference member there may be some risk for the vaginal device to sway and as such fall somewhat out of the perfect position inside of the vagina, e.g. during substantial movement. The shape of the right protruding end and left protruding end of the reference member may e.g. be ribbons which have widths that are smaller than the diameter of the longitudinal portion.

According to one specific embodiment of the present invention, the reference member has a left protruding end and a right protruding end, the right protruding end protruding 40-50 mm from the geometrical centre line of the longitudinal portion at the lower end and the left protruding end protruding 10-25 mm from the geometrical centre line of the longitudinal portion at the lower end. 40-50 mm, such as 40-45 mm, 45-50 mm, e.g. 45 mm, is a length interval of the right protruding end which may be suitable for an elevated fixation of the reference member. Moreover, 10-25 mm, such as 10-20 mm, 10-15 mm, 15-25 mm, 15-20 mm, e.g. 15 mm, is a length interval of the left protruding end of the reference member which is enough for achieving good fixation of the vaginal device inside of the vagina without any risk for any swaying during powerful movement by the user, but at the same time is short enough not to irritate the clitoris of the user. The reference member of the vaginal device according to the present invention functions as a means for insertion and pulling out the vaginal device.

The shape of the reference member may vary, but a suitable example is as a ribbon which has the same width or a thinner width than the longitudinal portion of the vaginal device according to the present invention. According to one specific embodiment, the reference member is concave. This means that both of the right protruding end and left protruding end of the reference member may have this concave shape. The possible concave shape of the right protruding end and possibly also the shorter left protruding end means that these ends bend somewhat upwards, that is in a direction going from the lower end of the longitudinal portion and upwards. The bending or curvature in this case is not very large, and the length from the lower end of the longitudinal portion, at the centre line, to a plane perpendicular to and intercepting the longitudinal portion and the tip of the right protruding end, at the centre line of the longitudinal portion, is about 5-30 mm, such as 10, 15, 20 or 25 mm or in between thereof. This concave shape of the reference member may increase the stability and fixation of the vaginal device during use.

Furthermore, the vaginal device according to the present invention may be provided with other additional features or means. According to one specific embodiment of the present invention, a pressure sensor is provided inside of the longitudinal portion at the upper end together with means for expansion of the vaginal device situated inside of the longitudinal portion. A pressure sensor may be provided together with means for expansion of the vaginal device so that when the pressure increases inside of the vagina, the vaginal device will expand somewhat to take care of the pressure wave, such as during sneezing or coughing, and as such increase the support to the urethra at these pressure increased situations. If a pressure sensor and means for expansion are provided inside of the vaginal device, the pressure sensor should be provided close to the upper end of the longitudinal portion so that the sensor will be able to sense an increase pressure wave coming from the abdomen as quick as possible. For example, the pressure sensor may be provided just beneath an outer thin membrane which membrane constitutes the surface of the vaginal device at the upper end thereof. The means for expansion may e.g. comprise an electromagnet and a coil. The electromagnet comprises an anchor and when an electric current is induced in the coil due to a pressure increase detection by the pressure sensor, the anchor is moved and as such "kicks" the supporting portion so that this portion further supports the urethra, through the vaginal wall, at the intended site.

Moreover, if a pressure sensor is provided, it may be of interest to have that provided inside of a longitudinal portion which has substantial length, in comparison, from the lower end to the upper, such as up to 90 mm, due to the fact that in such a case the pressure sensor will be situated to detect an increased pressure inside of the vagina as quick as possible. Moreover, the means for expansion of the vaginal device may be provided as different organs inside of the longitudinal portion, e.g. at least one organ situated inside of the longitudinal portion close to the at least one supporting portion so that the expansion is made largest at the site or sites giving the most effect thereof.

As mentioned, the vaginal device according to the present invention may be provided in a kit. According to one embodiment, there is provided a kit comprising the vaginal device according to the present invention and at least one pharmaceutical agent. Examples of possible pharmaceutical agents are oestrogen and alpha stimulators.

According to another specific embodiment, there is provided a kit comprising a hollow vaginal device according to the present invention and at least one introducible probe or rod matching the hollow vaginal device. The introducible plug, probe or rod may be of different type and have different objects. The introducible plug or rod may be provided to increase the diameter or hardness of the longitudinal portion. This may be accomplished by introducing a rod of e.g. plastic material having a high hardness in comparison to the material of the rest of the vaginal device inside of the hollow longitudinal portion. The rod may in this case e.g. have a length which is the same as the length of the hole of the longitudinal portion or e.g. a bit shorter. The introducible plug, rod or probe should of course have a diameter which suits the diameter of the hole of the hollow longitudinal portion. Moreover, as said, the thickness of the wall of the hollow longitudinal portion should be thin enough so that the properties of the introducible plug, rod or probe are possible to transfer to the longitudinal portion. The locking mechanism of the introducible rod, plug or probe, keeping it in place, may be of different sort, e.g. grooves on the rod, plug or probe that lock into recesses provided inside of longitudinal portion at the lower end thereof.

Another possible introducible organ is a shorter plug, which may function as a shock absorber inside of the hollow longitudinal portion due to the fact that an air filled hole is provided between the tip of the plug and the upper end of the hollow longitudinal portion.

Moreover, the introducible rod or plug may also be possible to vibrate. The vibrating rod is e.g. provided with a battery and an on and off switch for turning the vibration on and off. Another example of a vibrating rod according to the present invention is a rod where the vibration is turned on automatically by contraction of the pelvis by a user, such as during pelvic floor training. Such a vibrating rod may be turned off automatically after e.g. 5-10 s when the contraction is decaying. Such a vibrating rod may be an aid to facilitate muscle training for the urethral zoon.

Moreover, the introducible rod or plug may be provided to release at least one pharmaceutical agent which is intended to penetrate through the longitudinal portion of the vaginal device. In such a case, the longitudinal portion should be of a membrane-like material which is permeable for the intended at least one pharmaceutical agent.

According to another specific embodiment of the present invention, there is provided a kit as above, wherein the introducible probe is a probe for electric nerve stimulation of the urethra and the pelvic floor. The probe is intended to provide stimulation through electrodes placed on the longitudinal portion of the vaginal device or in combination with electrodes situated on the centre or the supporting portions of the device. Preferably, the electrodes are situated in the periphery of the supporting portions of the device. This stimulation should accomplish the provision of electric pulses of low voltage and by a frequency e.g. in the range of from 5 to 50 Hz, such as 50 Hz. The polarity of the voltage of the pulses should be shifted during the procedure and there is a non-operating time between the different pulses. The pulses provide a contraction of the urethral muscles which accomplish an increased support/pressure against the urethra, through the vaginal wall. Due to the fact that this stimulation gives a contraction of the urethral muscles, the procedure provides not only a support but in fact also a pressure on the urethra, through the vaginal wall and as such provides "automatic" perineal training. The electro-stimulation increases the urethral pressure and converts fast twitch fibers to slow twitch fibers in the striated muscles of the urethra during long term treatment. Slow twitch fibers have the possibility to keep a contraction during longer time compared with the fast twitch fibers and will in that way resemble the smooth muscles.

According to one specific embodiment of the present invention, there is provided a kit comprising a hollow vaginal device according to the present invention and at least one introducible probe or rod matching the hollow vaginal device, the kit optionally comprising at least one pharmaceutical agent, wherein the at least one introducible probe or rod is a probe for electric nerve stimulation or a rod which may vibrate.

DETAILED DESCRIPTION OF THE DRAWINGS

Figure 1:
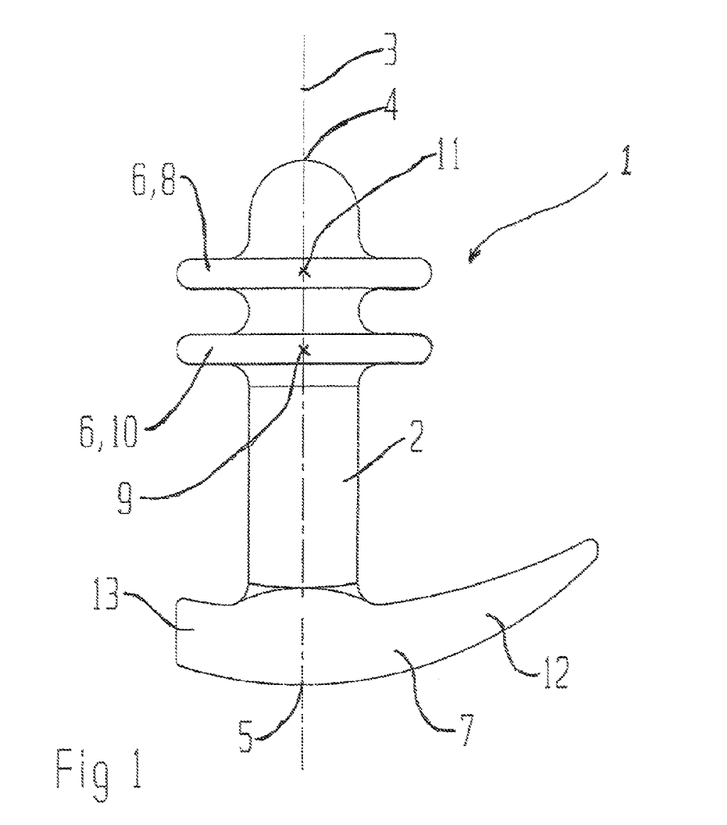
FIG. 1 shows a side view of a vaginal device according to the present invention.

FIG. 1 shows a vaginal device 1 according to the present invention. The vaginal device 1 comprises a longitudinal portion 2 having a geometrical centre line 3, an upper end 4 and a lower end 5. Moreover, the vaginal device 1 comprises at least one supporting portion 6 protruding from the longitudinal portion 2. In this case the vaginal device 1 according to the present invention has two circular supporting portions 6, one uppermost 8 having a centre 11 along the geometrical centre line 3 and one lowermost 10 having a centre 9 along the geometrical centre line 3, the supporting portions 6 protruding symmetrically around the longitudinal portion 2. The vaginal device 1 also comprises a reference member 7 protruding from the longitudinal portion 2 at the lower end 5. During use, the reference member 7 is fixated against the vaginal introitus, holding the vaginal device 1 securely fixated inside of a vagina and ensuring the two supporting portions 6 to support against the urethra, through the vaginal wall, at an intended site located between close to the maximal urethral pressure point and the bladder neck, preferably located at the maximal urethral pressure point. In this specific case, the reference member 7 has a right protruding end 12 and a left protruding end 13, the right protruding end 12 being intended to be fixated against the perineum by the user, and if done, the left protruding end 13 of the reference member is that end facing towards the opposite direction, that is towards the clitoris but not reaching the same.

The vaginal device 1 according to the present invention shown in FIG. 1 has a longitudinal portion having a circular cross section and a diameter of about 15 mm. Moreover, the diameters of the circular supporting portions 6 are in this specific case 35 mm. The reference member 7 is in this case concave and the right protruding end 12 protrudes about 40 mm from the geometrical centre line 3 at the lower end 5 of the longitudinal portion 2. The left protruding end 13 of the reference member 7 protrudes about 17.5 mm from the geometrical centre line 3 at the lower end 5 of the longitudinal portion 2. The reference member 7 in this case is a ribbon which has a thickness perpendicular to the geometrical centre line 3 of about 15 mm, that is the same thickness as the diameter of the longitudinal portion 2. Furthermore, the distance from the lower end 5 to the centre 9 of the lowermost of the two supporting portions 6, 10 is in this case about 45 mm along the geometrical centre line 3. The distance between the two supporting portions, from centre 9 to centre 11, is about 10 mm. The distance from the centre 11 of the uppermost supporting portion 6, 8 to the round upper end 4, at the geometrical centre line 3, is about 25 mm.

Naturally, the specific shapes and e.g. diameters of the different parts and portions of the vaginal device 1, and the distance between these parts and portions, may vary, and the values given above should only be seen as examples.

Figure 2:
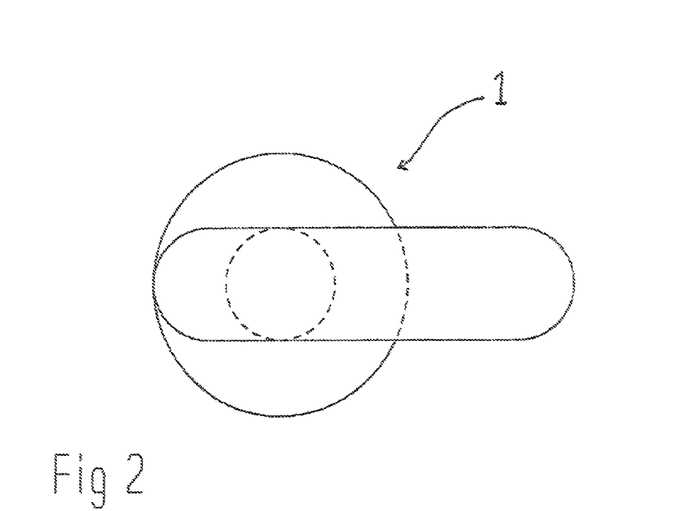
FIG. 2 shows a view of a vaginal device according to the present invention seen from the lower end of the longitudinal portion.

FIG. 2 shows the vaginal device 1 according to FIG. 1, but seen from below, that is seen from the lower end 5. The longitudinal portion 2 is shown as a dashed circle in the middle.

Figure 3:
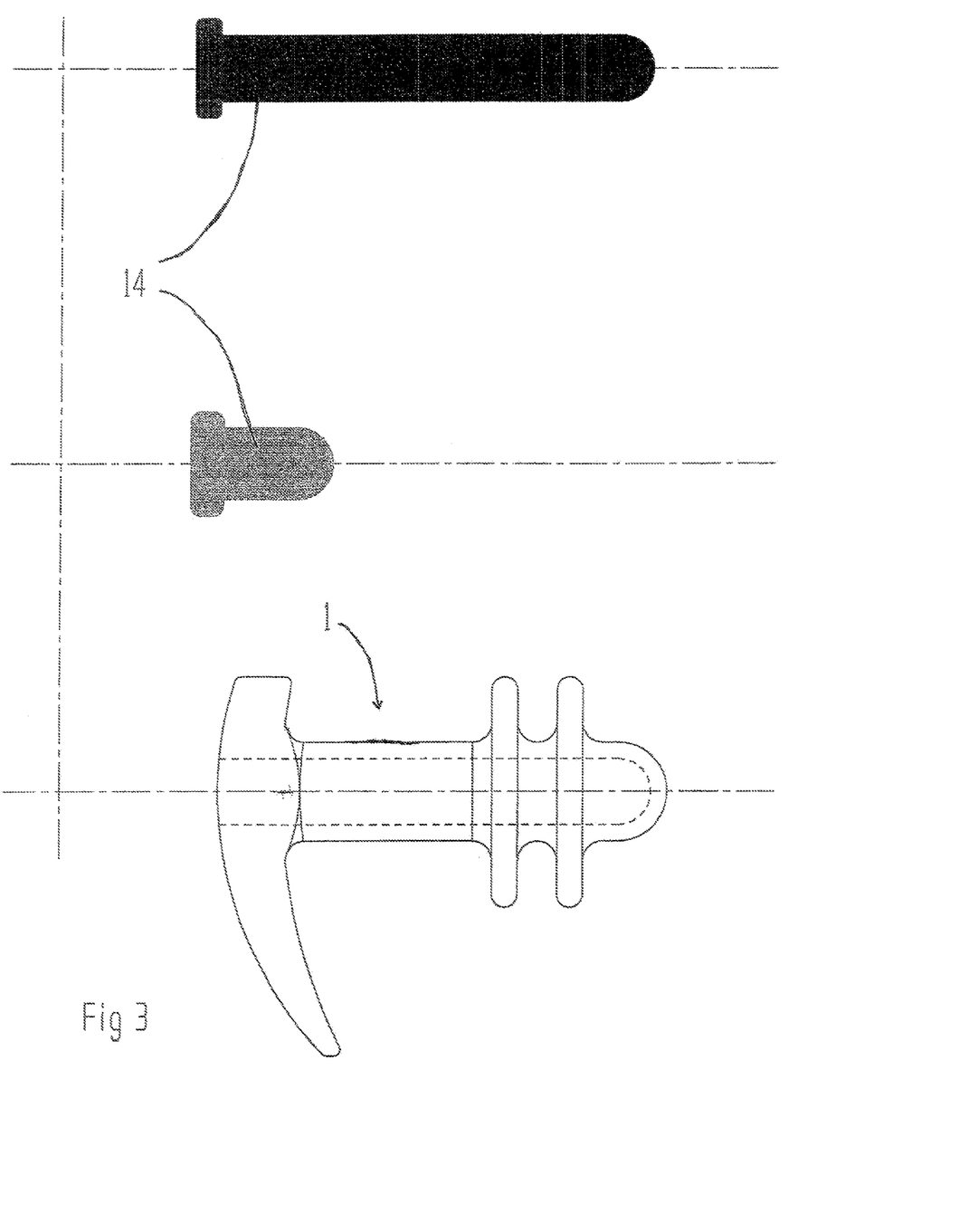
FIG. 3 shows a kit comprising a hollow vaginal device according to the present invention, seen from the side, as well as two different probes or rods which are introducible into the hollow vaginal device.

FIG. 3 shows a kit according to the present invention. The kit in this case comprises a hollow vaginal device 1, which has the same shape as the vaginal device according to FIG. 1, and two different types of rods 14. The hollowness of the vaginal device 1 is shown by the dashed line going from the lower end 5 and up to the upper end 4, but not through the same. The rods 14 are of different type. One of them are long in comparison and is e.g. intended to increase the diameter and/or hardness of the vaginal device 1 made of an elastic material of medical quality, to adjust the fit of the same inside of a vagina. The other rod 14 is a shorter plug, which may function as a shock absorber inside of the hollow longitudinal portion 2 due to the fact that an air filled hole is provided between the tip of the plug and the upper end 4 of the hollow longitudinal portion 2. There may of course be provided other types of rods also in a kit according to the present invention, such as a vibrating rod or a rod or plug 14 which may release at least one pharmaceutical agent which is intended to penetrate through the longitudinal portion 2 of the vaginal device 1. Furthermore, it is e.g. also possible to provide an introducible probe which is a probe for electric nerve stimulation of the urethra and the pelvic floor in a kit according to the present invention.

Pilot Study of Vaginal Devices According to the Present Invention

The effects of different vaginal devices or "vaginal plugs" according to the present invention have been investigated on urinary stress incontinent women. First 8 women with urinary stress incontinence were examined with a vaginal device according to the invention having a reference member in the form of a base plate protruding in all directions from the longitudinal portion. The vaginal devices were made of soft silicone rubber material of medical quality. Two different sizes were used, called M35 and M40, both having a reference member as a plate protruding outside the labia majorae and minorae in anterior-posterior direction and having two supporting portions protruding separately from each other along the longitudinal portion and, said supporting portions protruding around the longitudinal portion and having circular cross sections in a plane perpendicular to the longitudinal portion, where the two different vaginal device had supporting portions with diameters of 35 mm and 40 mm, respectively. The diameter of the longitudinal portion having a circular cross section was about 15 mm. The vaginal devices had an upper end with a round shape and with a distance of about 15 mm to the uppermost circular supporting portion, at the geometrical centre line. Moreover, the distance between the two supporting portions or supporting members was about 10 mm at the geometrical centre line. The full length of the vaginal device, from the lower end to the upper end at the geometrical centre line, was about 70 mm.

As an effort to increase the fixation of the vaginal device, the reference member was cut giving a reference member, which no longer was in the form of a base plate. Instead the new shape of the reference member became a one side cut anchor ribbon actually only protruding in a right and left direction from the longitudinal portion, where e.g. the left protruding end protruded a shorter distance from the geometrical centre line than the right protruding end, or vice versa. The reference member was still curved upward, just as the base plate, in the right and left direction from the geometrical centre line. These cut versions of the vaginal device according to the invention was further used in the investigations.

Women with urinary stress incontinence were tested with this reference member cut version of the vaginal device according to the present invention. 30 women were tested with the device having size M35, 2 women were tested with the device having size M40 and 1 woman was tested with a device having size M35 but not having a reference member at all. This last version is a device which is not intended to be part of the scope according to the present invention and which may be seen as a comparing device. The lack of a reference member seemed to give an inferior support of the mid-urethra compared with the cut version and was abandoned.

Prior to the investigation, the women had been objectively diagnosed as having a genuine urinary stress incontinence by urodynamic investigation. No women with urge or mixed incontinence were included in the investigation.

One woman of the 30 tested with the device of size M35 was excluded due to the fact that the device was too wide and hence not possible to insert into the vagina.

The test method was performed according to the following. After the women had given their oral consent, the vaginal device or plug was inserted into the vagina together with some glide agent. A dry incontinence sanitary napkin was weighed. Thereafter the incontinence sanitary napkin was applied and was fixated with net pants. The women "springboard jumped" up and down 20 times with a full bladder, with legs going in an out. The leakage in the sanitary napkin was weighed on an electronic weighing machine. The vaginal device according to the present invention was removed and a new incontinence sanitary napkin was weighed and applied. 20 new jumps were made in the same way as above. The second sanitary napkin was weighed and the leakage with and without the vaginal device according to the present invention was calculated. Cystometrical bladder capacity was estimated before the test and registered and micturated volume was notated after the test.

Results (Summary) of the Investigation of the 30 Women Tested for M35 Type Device.

Below the results of the tests are summarised. As mentioned, one woman was excluded because of a too narrow vagina for the M35 type device.

13 of the 29 women (45%) tested with the vaginal device obtained a totally dry incontinence sanitary napkin after the jump test;

26 of the 29 women (90%) obtained a reduced leakage when using the vaginal plug according to the present invention (comparison of the weight of the incontinence sanitary napkin when using the plug vs. not using the plug after the jump test);

20 of the 29 women (69%) had at least a 50% leakage reduction;

the average reduction of the leakage was 58%;

Conclusions of the Performed Investigation

The vaginal device according to the present invention reduces the urine leakage in women suffering from urinary stress incontinence to a great extent. In almost half the investigated cases the urine leakage was eliminated.

The invention claimed is:

1. A vaginal device of an elastic material, said vaginal device comprising a longitudinal portion having a geometrical centre line, an upper end and a lower end and which vaginal device is intended to be inserted and securely fixated inside of a vagina, the upper end of the vaginal device being innermost in the vagina during use, to support against the urethra, through the vaginal wall, to prevent urinary stress incontinence in a woman, wherein the vaginal device comprises at least one supporting portion protruding from the longitudinal portion, said at least one supporting portion being intended to support against the urethra, through the vaginal wall, at a site located between close to a maximal urethral pressure point and the bladder neck, and wherein the vaginal device also comprises a reference member protruding from the longitudinal portion at the lower end and the protruding reference member has a non-tapered left protruding end and a tapered right protruding end and the tapered right protruding end protrudes further from the geometrical centre line than the non-tapered left protruding end, which reference member during use is adapted to be fixated against the vaginal introitus, wherein the tapered right protruding end is adapted to be fixated against the perineum, ensuring the vaginal device securely fixated inside of the vagina and ensuring said at least one supporting portion is adapted to support against the urethra, through the vaginal wall, at the site located between close to the maximal urethral pressure point and the bladder neck, and wherein the tapered right protruding end extends outward from the geometrical centre line further than the at least one supporting portion extends outward from the geometrical centre line.

2. The vaginal device according to claim 1, wherein the elastic material is chosen from the group consisting of polyurethane, silicone rubber, latex rubber, polystyrene copolymer materials and natural rubber, or combinations thereof.

3. The vaginal device according to claim 1, wherein the at least one supporting portion is resilient in a radial direction.

4. The vaginal device according to claim 1, wherein the at least one supporting portion protrudes circumferentially around the longitudinal portion at the upper end of the device.

5. The vaginal device according to claim 1, wherein the vaginal device comprises at least one perforation going through the at least one supporting portion.

6. The vaginal device according to claim 1, wherein the at least one supporting portion protrudes circumferentially around the longitudinal portion at the upper end of the device and is substantially circular in a plane perpendicular to the geometrical centre line.

7. The vaginal device according to claim 1, wherein the at least one supporting portion protrudes circumferentially around the longitudinal portion at the upper end of the device, is substantially circular in a plane perpendicular to the geometrical centre line and has a diameter of 25-45 mm.

8. The vaginal device according to claim 1, wherein the longitudinal portion is circular and has a diameter of 10-20 mm.

9. The vaginal device according to claim 1, wherein the longitudinal portion has a length of 50-90 mm from the lower end to the upper end.

10. The vaginal device according to claim 1, wherein the at least one supporting portion has an uppermost supporting portion; and wherein the upper end has a round shape and has a distance of 10-45 mm to the uppermost supporting portion of the at least one supporting portion, at the geometrical centre line.

11. The vaginal device according to claim 1, wherein the longitudinal portion has a lower end; wherein the at least one supporting portion has a centre; and wherein the lower end of the longitudinal portion, at the geometrical centre line, has a distance to the centre of the at least one supporting portion, at the geometrical centre line, of 20-55 mm.

12. The vaginal device according to claim 1, wherein the longitudinal portion is hollow from the lower end towards the upper end, but not through the upper end.

13. The vaginal device according to claim 1, wherein the at least one supporting portion has a thickness of 3-5 mm.

14. The vaginal device according to claim 1, wherein the vaginal device comprises at least two supporting portions protruding from the longitudinal portion, said at least two supporting portions protruding separately from each other along the longitudinal portion and all of the at least two supporting portions being intended to support against the urethra, through the vaginal wall, at sites located between close to the maximal urethral pressure point and the bladder neck.

15. The vagina device according to claim 14, wherein the two supporting portions, each comprising a lowermost supporting portion and an uppermost supporting portion, protruding from the longitudinal portion and the longitudinal portion comprises a lower end, said at least two supporting portions protruding separately from each other along the longitudinal portion and both of the at least two supporting portions being intended to support against the urethra, through the vaginal wall, at two sites located between close to the maximal urethral pressure point and the bladder neck, and wherein the lower end of the longitudinal portion, at the geometrical centre line, to the lowermost of the two supporting portions, at the geometrical centre line, has a distance of 20-50 mm, and the lower end of the longitudinal portion, at the geometrical centre line, to the uppermost of the two supporting portions, at the geometrical centre line, has a distance of 50-65 mm.

16. The vaginal device according to claim 1, wherein the tapered right protruding end protrudes at least 40 mm from the geometrical centre line of the longitudinal portion at the lower end and the non-tapered left protruding end protrudes below 25 mm from the geometrical centre line of the longitudinal portion at the lower end.

17. The vaginal device according to claim 1, wherein the tapered right protruding end protrudes 40-50 mm from the geometrical centre line of the longitudinal portion at the lower end and the non-tapered left protruding end protrudes 10-25 mm from the geometrical centre line of the longitudinal portion at the lower end.

18. The vaginal device according to claim 1, wherein the reference member is concave.

19. The vaginal device according to claim 1, wherein a pressure sensor is provided inside of the longitudinal portion at the upper end together with means for expansion of the vaginal device situated inside of the longitudinal portion.

20. A kit comprising the vaginal device according to claim 1, and at least one pharmaceutical agent.

21. A kit comprising a hollow vaginal device according to claim 12, and at least one introducible probe or rod matching the hollow vaginal device.

22. A kit comprising a hollow vaginal device according to claim 12, and at least one introducible probe or rod matching the hollow vaginal device, the kit optionally comprising at least one pharmaceutical agent, wherein the at least one introducible probe or rod is a probe for electric nerve stimulation or a rod which may vibrate.

23. A vaginal device of an elastic material, said vaginal device comprising a longitudinal portion having a geometrical centre line, an upper end and a lower end and which vaginal device is intended to be inserted and securely fixated inside of a vagina, the upper end of the vaginal device being innermost in the vagina during use, to support against the urethra, through the vaginal wall, to prevent urinary stress incontinence in a woman, wherein the vaginal device comprises at least one supporting portion protruding from the longitudinal portion, said at least one supporting portion being intended to support against the urethra, through the vaginal wall, at a site located between close to a maximal urethral pressure point and the bladder neck, and wherein the vaginal device also comprises a reference member protruding from the longitudinal portion at the lower end and the protruding reference member has a non-tapered left protruding end and a tapered right protruding end and the tapered right protruding end protrudes further from the geometrical centre line than the non-tapered left protruding end, which reference member during use is adapted to be fixated against the vaginal introitus, wherein the tapered right protruding end is adapted to be fixated against the perineum, ensuring the vaginal device securely fixated inside of the vagina and ensuring said at least one supporting portion is adapted to support against the urethra, through the vaginal wall, at the site located between close to the maximal urethral pressure point and the bladder neck, and wherein the tapered right protruding end is curved toward the at least one supporting potion.

24. A vaginal device of an elastic material, said vaginal device comprising a longitudinal portion having a geometrical centre line, an upper end and a lower end and which vaginal device is intended to be inserted and securely fixated inside of a vagina, the upper end of the vaginal device being innermost in the vagina during use, to support against the urethra, through the vaginal wall, to prevent urinary stress incontinence in a woman, wherein the vaginal device comprises at least one supporting portion protruding from the longitudinal portion, said at least one supporting portion being intended to support against the urethra, through the vaginal wall, at a site located between close to a maximal urethral pressure point and the bladder neck, and wherein the vaginal device also comprises a reference member protruding from the longitudinal portion at the lower end and the protruding reference member has a non-tapered left protruding end and a tapered right protruding end and the tapered right protruding end protrudes further from the geometrical centre line than the non-tapered left protruding end, which reference member during use is adapted to be fixated against the vaginal introitus, wherein the tapered right protruding end is adapted to be fixated against the perineum, ensuring the vaginal device securely fixated inside of the vagina and ensuring said at least one supporting portion is adapted to support against the urethra, through the vaginal wall, at the site located between close to the maximal urethral pressure point and the bladder neck, and wherein the longitudinal portion is a solid body of elastic material, free of a central shaft.

* * * * *

UNITED STATES PATENT AND TRADEMARK OFFICE
CERTIFICATE OF CORRECTION

PATENT NO. : 9,445,882 B2
APPLICATION NO. : 13/141226
DATED : September 20, 2016
INVENTOR(S) : Lars Henriksson Page 1 of 1

It is certified that error appears in the above-identified patent and that said Letters Patent is hereby corrected as shown below:

In the Specification

In Column 1 at Line 3 (approx.), After "U.S.C." insert --§--.

In Column 1 at Line 7 (approx.), After "U.S.C." insert --§--.

In Column 5 at Line 62, Change "to" to --too--.

In Column 14 at Line 36, Change "58%;" to --58%.--.

In the Claims

In Column 15 at Line 62, In Claim 15, change "vagina" to --vaginal--.

In Column 17 at Line 3, In Claim 23, change "potion." to --portion.--.

Signed and Sealed this
Second Day of May, 2017

Michelle K. Lee
*Director of the United States Patent and Trademark Office*